US00PP31007P3

(12) United States Plant Patent
Wright et al.

(10) Patent No.: US PP31,007 P3
(45) Date of Patent: Nov. 5, 2019

(54) BLUEBERRY PLANT NAMED 'C08-141'

(50) Latin Name: ***Vaccinium corymbosum* hybrid**
Varietal Denomination: C08-141

(71) Applicants: CostaExchange Pty Ltd., Corindi, New South Wales (AU); Florida Foundation Seed Producers, Inc., Marianna, FL (US)

(72) Inventors: Gary Wright, Arrawarra (AU); Paul Lyrene, Greenwood, FL (US)

(73) Assignee: Fall Creek Farm & Nursery, Inc., Lowell, OR (US)

( * ) Notice: Subject to any disclaimer, the term of this patent is extended or adjusted under 35 U.S.C. 154(b) by 0 days.

(21) Appl. No.: 15/932,971

(22) Filed: May 31, 2018

(65) Prior Publication Data

US 2018/0352692 P1 Dec. 6, 2018

Related U.S. Application Data

(60) Provisional application No. 62/603,492, filed on Jun. 1, 2017.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
See application file for complete search history.

(56) References Cited

U.S. PATENT DOCUMENTS

| | | | |
|---|---|---|---|
| PP12,165 | P2 | 10/2001 | Lyrene |
| PP20,642 | P2 | 1/2010 | Wright |
| PP20,695 | P2 | 2/2010 | Wright et al. |
| PP26,917 | P3 | 7/2016 | Wright et al. |

OTHER PUBLICATIONS

UPOV hit over blueberry plant named, 'C08-141', AU PBR 6044, filed Sep. 7, 2017.*

* cited by examiner

*Primary Examiner* — Anne Marie Grunberg
(74) *Attorney, Agent, or Firm* — Plant & Planet Law Firm

(57) ABSTRACT

The new blueberry plant variety 'C08-141' is provided. 'C08-141' is a commercial variety intended for the fresh market. The variety is produced from a cross of 'FL00-057' and 'C99-042', which can be distinguished by its outstanding features.

5 Drawing Sheets

Latin name of the genus and species:
Genus—*Vaccinium.*
Species—*corymbosum* hybrid.
Variety denomination: The new blueberry plant claimed is of the variety denominated 'C08-141'.

BACKGROUND OF THE INVENTION

The new variety 'C08-141' was selected from a population of seedlings derived from crossing the blueberry varieties known as 'FL00-057' (seed parent) (not patented)) and the variety known as 'C99-042' (U.S. Plant Pat. No. 20,695) (pollen parent). The cross was made in 2006 in Florida, USA and the seed was sown and grown on in Corindi Beach, NSW, Australia. The new variety was selected in 2008 from among plants located on land at Corindi Beach and assigned the breeding code 'C08-141'. Plants of 'C08-141' were propagated by cuttings for further evaluation and resulted to be uniform and stable. The new variety showed distinctive traits such as evergreen, vigorous, good flavor and firm fruit.

SUMMARY OF THE INVENTION

The new variety 'C08-141' was originated from a cross of 'FL00-057' (seed parent) and the variety known as 'C99-042' in 2006 in Florida, USA. The pollen parent is characterized by an early to mid-season timing of fruit ripening, it is evergreen, its fruit is of high firmness.

The new blueberry variety resulted from seedlings produced in a controlled breeding programme. The cross was made in 2006 in Florida, USA and the seed was sown and grown on in Corindi Beach, NSW, Australia.

The new variety was selected in 2008 from among plants located on land at Corindi Beach and has since been named 'C08-141'. Since then plants of 'C08-141' were propagated by cuttings for further evaluation and resulted to be uniform and stable. Asexual reproduction of the new variety 'C08-141' by cutting propagation since 2008 at Corindi Beach, NSW, Australia has demonstrated that the new variety reproduces true to type plants.

The new variety was selected in 2008 as a single plant within a population of seedlings resulting from controlled cross of *Vaccinium* varieties. The seedling population was planted in an experimental block in the field at Corindi Beach, NSW, Australia and the selection of the new variety took place in the same block. Selection criteria were a combination of early to mid-season, low chilling requirement, strong vigour, non-deciduous type of plant (evergreen), large fruit size, good fruit flavor and firm fruit. The new variety was subsequently evaluated for a number of years at the commercial farm at Corindi Beach, NSW, Australia.

The following characteristics of the new variety have been repeatedly observed and can be used to distinguish 'C08-141' as a new and distinct variety of *Vaccinium corymbosum* hybrid:

1. Non-deciduous (Evergreen)
2. Early to medium season crop
3. Strong plant vigour
4. Low chilling requirement
5. Large fruit size
6. Good fruit flavor
7. Firm fruit The new variety differed from the male parent 'C99-042' in that 'C08-141' has a higher vigour and a larger fruit size. The new blueberry variety 'C08-141' has maintained its distinguished characteristics throughout successive asexual propagation. The variety has been repeatedly asexually reproduced thought softwood cuttings in NSW, Australia and the clones are phenotypically identical to the original plant.

BRIEF DESCRIPTION OF THE DRAWINGS

The accompanying photographic illustration shows typical specimens in full color of the foliage and fruit of the new variety 'C08-141'. The colors are as nearly true as is reasonably possible in a color representation of this type.

Figure 1:
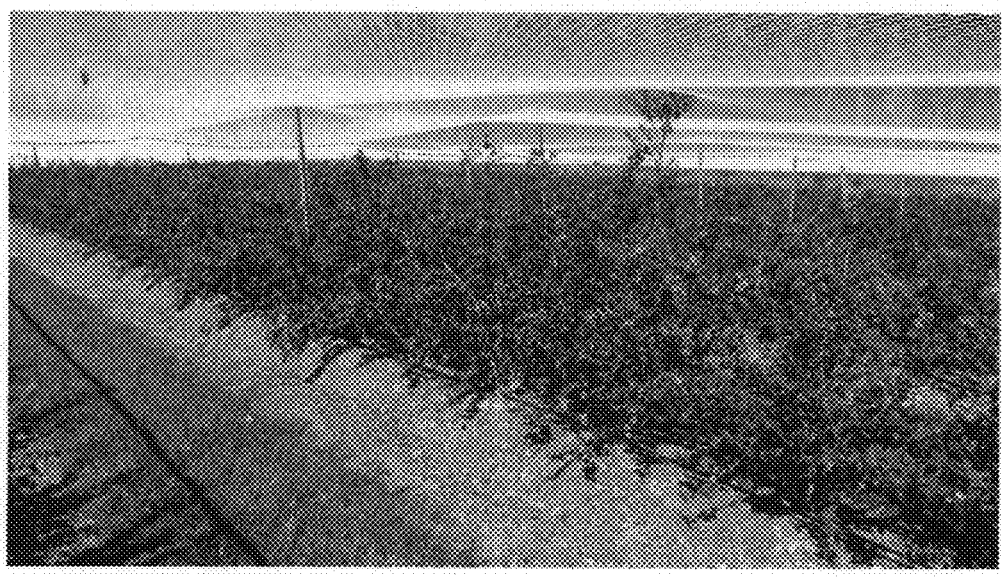
FIG. 1 is a photograph of the new variety 'C08-141', demonstrating a four year old plant's upright habit and the strong vigour.
Figure 2:
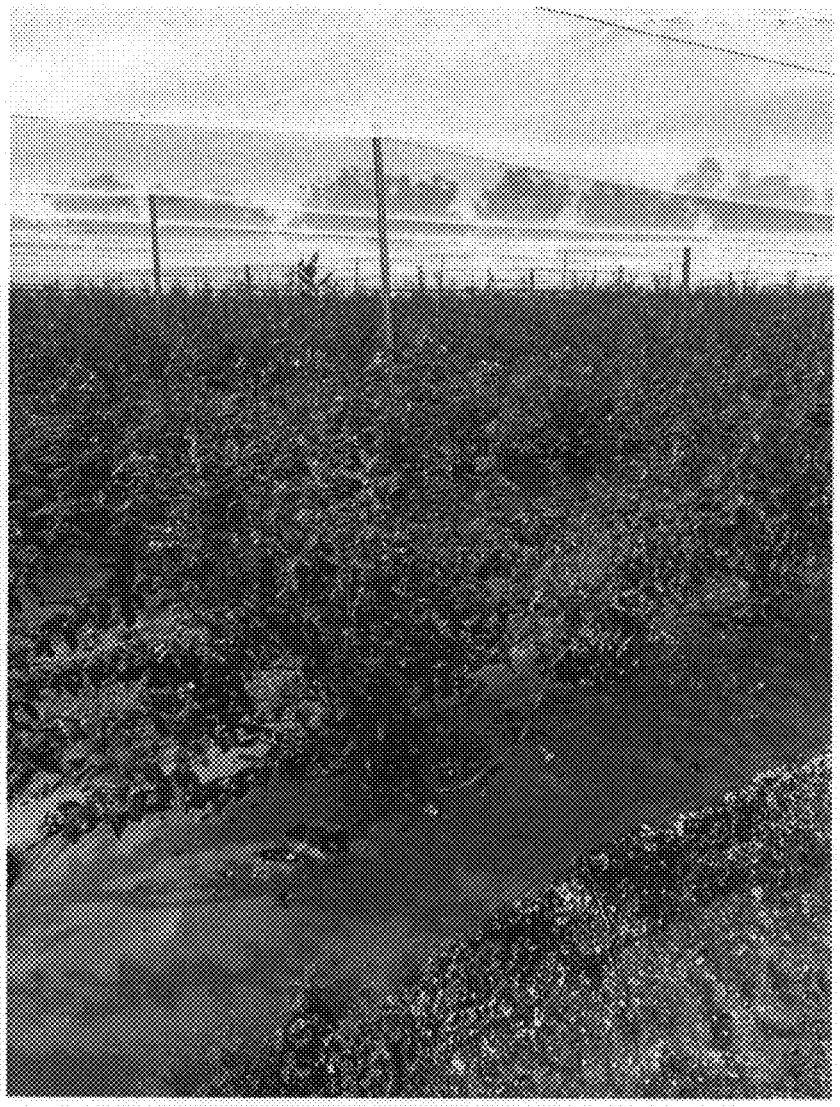
FIG. 2 is a photograph of the new variety 'C08-141', showing the typical red coloration of the wood during the winter time on a four year old plant.
Figure 3:
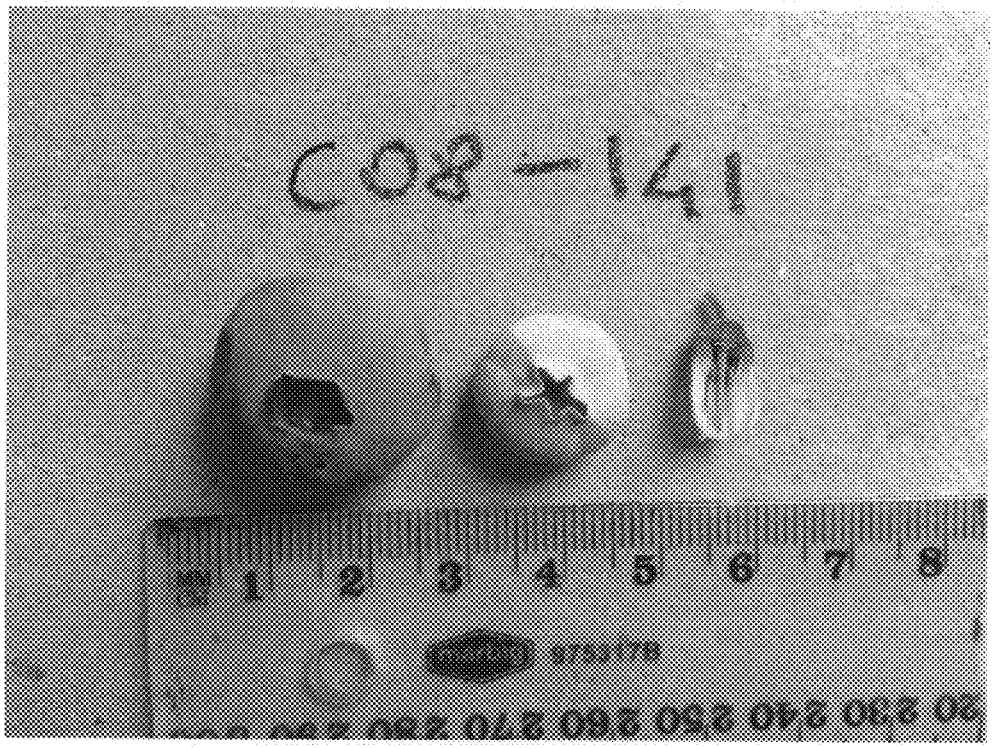
FIG. 3 is a photograph of the mature fruit, green fruit and flower on a four year old plant of the new variety 'C08-141'.
Figure 4:
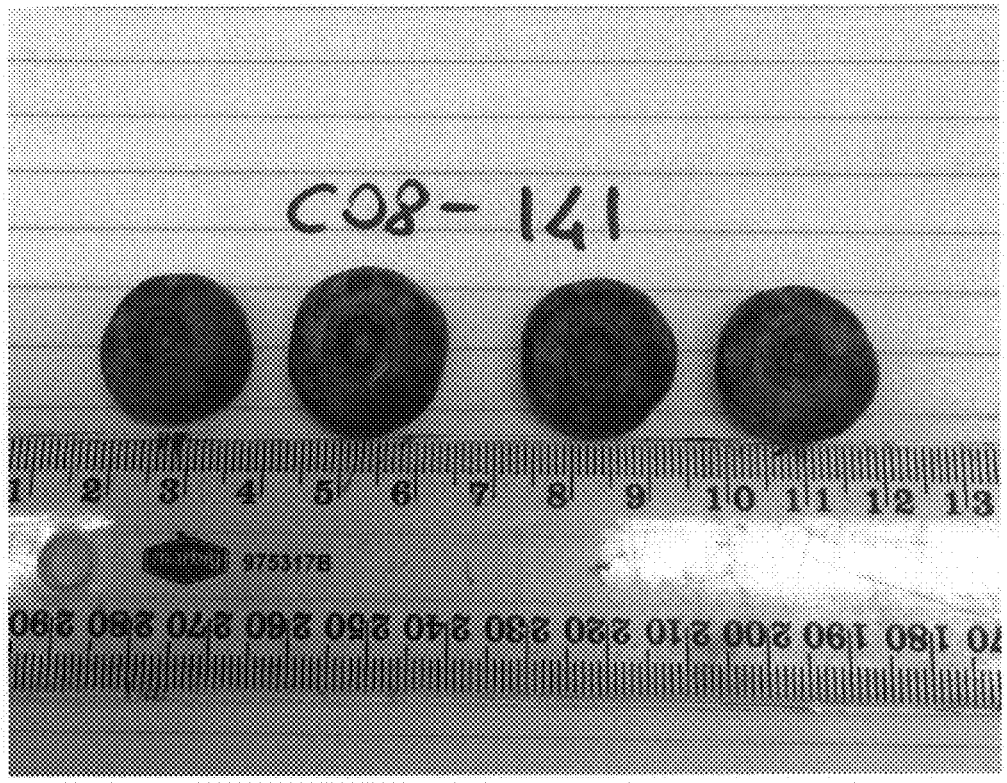
FIG. 4 is a photograph showing the large fruit size of the new variety 'C08-141' on a four year old plant.
Figure 5:
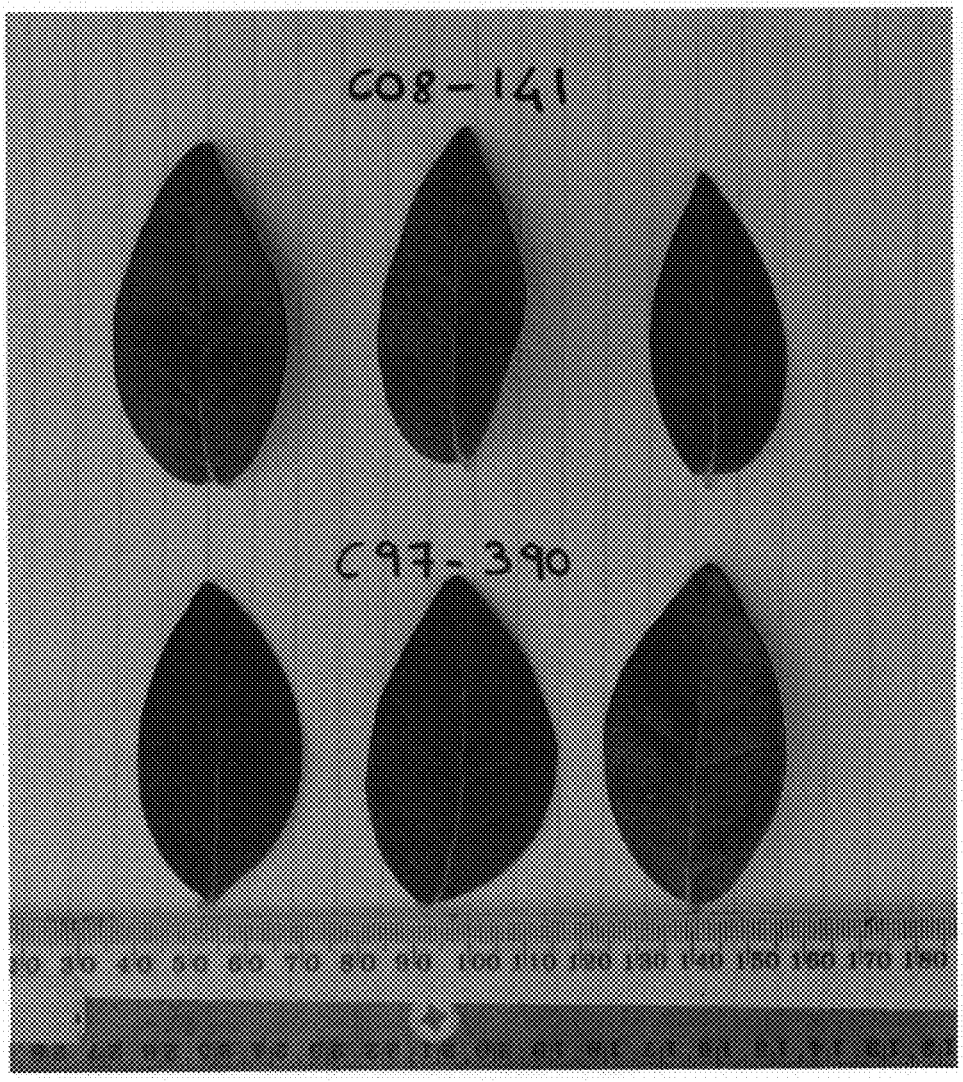
FIG. 5 is a photograph of the typical elliptic leaf of the new variety 'C08-141' on a four year old plant.

The colors in the photographs are as close as possible with the photographic and printing technology utilized. The color values cited in the detailed botanical description accurately describe the colors of the new blueberry.

DETAILED BOTANICAL DESCRIPTION

The following detailed description sets forth the distinctive characteristics of 'C08-141'. The data which define these characteristics were collected from asexual reproductions of the original selection. Dimensions, sizes, colors, and other characteristics are approximations and averages set forth as accurately as possible. The plant history was taken on plants approximately 5 years of age, and the descriptions relate to plants grown in the field in Corindi Beach, NSW, 2456 Australia. Descriptions of fruit characteristics were made on fruit grown in Corindi Beach, NSW, 2456 Australia. Color designations are from R.H.S. Chart—edition 2007.

Classification:

a. *Family*.—Ericaceae.
b. *Genus*.—*Vaccinium*.
c. *Species*.—*Corymbosum* hybrid.
d. *Common name*.—Blueberry.

Parentage:

*Female parent*.—Unpatented selection 'FL00-057'.
*Male parent*.—'C99-042' (U.S. Plant Pat. No. 20,695).

Market class: Fresh market.

PLANT

General:

a) *Parentage*.—FL00-057 x C99-042.
b) *Plant height*.—1.5 m.
c) *Plant width*.—1.0 m.
d) *Growth habit*.—Upright.
e) *Growth*.—Vigorous.
f) *Productivity*.—Medium to high yield.
g) *Cold hardiness*.—Low chill.
h) *Cold tolerance*.—Low.
i) *Chilling requirement*.—Low, estimated between 150 and 300 hours.
j) *Tolerance to disease*.—Tolerant to leaf rust.
k) *Leafing*.—Overall medium to high and plant retains leaves during the winter.
l) *Twigginess*.—Low.
m) *Fruiting type*.—On one-year old and current season's shoots.

STEM

General:

a) *Suckering tendency*.—Medium.
b) *Mature cane color*.—Between greyed green 197c and green brown N199B.
c) *Mature cane length*.—Average 0.6 m.
d) *Mature cane width*.—Average 8.3 mm.
e) *Bark texture*.—Medium.
f) *Fall color on new shoots*.—Greyed purple 185a.
g) *Surface texture of new wood*.—Smooth.
h) *Internode length on strong, new shoots*.—25.1 mm.
i) *Fruiting wood*.—146.4 cm in length.

FOLIAGE

General:

a) *Time of beginning of leaf bud burst*.—Early (August in Corindi, NSW, Australia).
b) *Leaf color* (*top side*).—Green group 139 A.
c) *Leaf color* (*under side*).—Green group 138C.
d) *Leaf arrangement*.—Alternate.
e) *Leaf shape*.—Elliptic.
f) *Leaf margins*.—Entire.
g) *Undulation of margin*.—Weak.
h) *Leaf venation*.—Reticulate.
i) *Leaf apices*.—Acute.
j) *Leaf bases*.—Rounded.
k) *Leaf length*.—68 mm.
l) *Leaf width*.—27.6 mm.
m) *Leaf length/width ratio*.—2.10.
n) *Leaf nectarines*.—Absent.
o) *Pubescence of upper side*.—Absent.
p) *Pubescence of lower side*.—Absent.
q) *Cross sectional profile*.—Flat.
r) *Longitudinal profile*.—Straight.
s) *Attitude*.—Horizontal.

Petioles:

a) *Length*.—Average 4.1 mm.
b) *Width*.—Average 1.5 mm.
c) *Color*.—Yellow green N144D.

FLOWERS

General:

a) *Time of beginning of flowering*.—Medium.
b) *Time of* 50% *anthesis*.—On average it is around the $2^{nd}$ of August.
c) *Flower shape*.—Urceolate.
d) *Flower bud density*.—Sparse to medium.
e) *Flower fragrance*.—No.

Corolla:

a) *Color*.—155C.
b) *Length*.—10.1 mm.
c) *Width*.—9.5 mm.
d) *Aperture width*.—5.12 mm.
e) *Anthocyanin coloration of corolla*.—Absent.
f) *Corolla ridges*.—Present.
g) *Protrusion of stigma*.—Absent.

Inflorescence:

a) *Length*.—20.13 mm
b) *Diameter*.—22.8 mm.
c) *Length of peduncle*.—10.6 mm.
d) *Surface texture of peduncle*.—Smooth.
e) *Color of peduncle*.—Yellow-green group 145B with greyed-red group 178B on top.
f) *Length of pedicel*.—7.6 mm.
g) *Surface texture of pedicel*.—Smooth.
h) *Color of pedicel*.—Yellow green group 145B.
i) *Number of flowers per cluster*.—4.4.
j) *Flower cluster density*.—Sparse to medium.

Calyx (with sepals):

a) *Diameter*.—5.9 mm.
b) *Color* (*sepals*).—Green group 138C.
c) *Fruit attitude of the sepals*.—Semi-erect.
d) *Type of sepals*.—Incurving.
e.) *Diameter of the fruit calyx basin*.—Medium.

Stamen:

a) *Length*.—7.6 mm.
b) *Number per flower*.—10.
c) *Filament color*.—Yellow-green group 145B.
d) *Style*.—Length — 8.9 mm.
e) *Color*.—Yellow-green group N144C.

Pistil:

a) *Length*.—11.3 mm.
b) *Ovary color* (*exterior*).—Green group 138B.

Anther:

a) *Length*.—4.8 mm.
b) *Number*.—10.
c) *Color*.—Greyed-orange group 165B.

Pollen:

a) *Abundance*.—Abundant.
b) *Color*.—Yellow group 4D.
c) *Self-compatibility*.—Overall good, with decent fruit sizes, around 2 g.

FRUIT

General:

a) *Time of fruit ripening*.—Early to medium.
b) *Time of* 50% *maturity*.—On average on the $30^{th}$ of September.
c) *Fruit development period*.—60 days.
d) *Cluster density*.—Medium (3-6 berries per cluster).
e) *Unripe fruit color*.—Light to medium, similar to green group 143C.
f) *Ripe berry color*.—Blue group 102A.
g) *Berry surface wax abundance*.—Strong.
h) *Berry flesh color*.—Yellow-green group 145C.
i) *Berry weight*.—On average 3.1 g.
j) *Berry height from calyx to scar*.—13.5 mm.
k) *Berry diameter*.—20.3 mm.
l) *Berry shape*.—Oblate.
m) *Fruit stem scar*.—Dry.
n) *Sweetness when ripe*.—Medium (11.2 Brix).
o) *Firmness when ripe*.—Firm to very firm (251 g/mm).
p) *Acidity when ripe*.—Medium (0.45%).
q) *Storage quality*.—Long shelf life.
r) *Suitability for mechanical harvesting*.—Not tested.
s) *Self-fruitfulness*.—High.
t) *Uses*.—Fruit to be hand harvested for fresh market.

SEED

General:

a) *Seed abundance in fruit*.—Medium to low, on average 11 seeds per fruit.
b) *Seed color*.—Greyed orange 165B.
c) *Seed length*.—1.45 mm.

COMPARISON BETWEEN PARENTAL AND COMMERCIAL CULTIVARS

TABLE 1

Distinctive characteristic of the new variety and comparison with similar varieties. The female parent 'FL00-057' is characterized by its good vigor and high yield of medium-large fruit.

| Characteristic | C08-141 (not patented) | C03-158 (U.S. Pat. Application No. 13/999,286) | C99-042 (not patented) | Emerald (U.S. Plant Pat. No. 12,165) |
|---|---|---|---|---|
| Soluble solid content (%) | 11.2 | 11.4 | 13.1 | 11.6 |
| Titratable acidity (%) | 0.45 | 0.4 | 0.3 | 0.5 |
| Fruit weight (g) | 3.1 | 2.5 | 1.9 | 3.0 |
| Fruit firmness (g/mm) | 251 | 240 | 272 | 238 |
| Plant habit | Upright | Upright | Semi-upright to spreading | Spreading |
| Time of fruit ripening | Early to medium | Mid-season | Early to medium | Mid to late |

| Characteristic | C97-390 (U.S. Plant Pat. No. 20,642) | Star (not patented) | Snowchaser (not patented) |
|---|---|---|---|
| Soluble solid content (%) | 12.2 | 13.1 | 14.3 |
| Titratable acidity (%) | 0.3 | 0.4 | 0.5 |
| Fruit weight (g) | 2.0 | 1.9 | 1.7 |
| Fruit firmness (g/mm) | 219 | 212 | 192 |
| Plant habit | Semi-upright | Strongly upright to upright | Semi-upright |
| Time of fruit ripening | Early | Late | Very early |

The invention claimed is:

1. A new and distinct variety of blueberry plant named 'C08-141', substantially as illustrated and described herein.

* * * * *